(12) United States Patent
Yamamoto (10) Patent No.: US 10,323,265 B2
(45) Date of Patent: Jun. 18, 2019

(54) RAPID AND HIGH-SENSITIVE BACTERIA DETECTION

(71) Applicant: KONICA MINOLTA LABORATORY U.S.A., INC., San Mateo, CA (US)

(72) Inventor: Noriaki Yamamoto, Tokyo (JP)

(73) Assignee: KONICA MINOLTA LABORATORY U.S.A., INC., San Mateo, CA (US)

( * ) Notice: Subject to any disclaimer, the term of this patent is extended or adjusted under 35 U.S.C. 154(b) by 0 days.

(21) Appl. No.: 15/564,425

(22) PCT Filed: Jun. 20, 2016

(86) PCT No.: PCT/US2016/038440
§ 371 (c)(1),
(2) Date: Oct. 4, 2017

(87) PCT Pub. No.: WO2016/209777
PCT Pub. Date: Dec. 29, 2016

(65) Prior Publication Data
US 2018/0135094 A1  May 17, 2018

Related U.S. Application Data

(60) Provisional application No. 62/185,473, filed on Jun. 26, 2015.

(51) Int. Cl.
| | | |
|---|---|---|
| *C12Q 1/04* | (2006.01) | |
| *C09K 11/02* | (2006.01) | |
| *C09K 11/06* | (2006.01) | |
| *C09K 11/58* | (2006.01) | |
| *G01N 21/64* | (2006.01) | |
| *C12M 1/34* | (2006.01) | |
| *G01N 33/533* | (2006.01) | |
| *G01N 33/542* | (2006.01) | |
| *G01N 33/569* | (2006.01) | |
| *G01N 21/07* | (2006.01) | |
| *G01N 21/77* | (2006.01) | |

(52) U.S. Cl.
CPC .............. *C12Q 1/04* (2013.01); *C09K 11/02* (2013.01); *C09K 11/06* (2013.01); *C09K 11/58* (2013.01); *C12M 41/36* (2013.01); *G01N 21/648* (2013.01); *G01N 21/6428* (2013.01); *G01N 33/533* (2013.01); *G01N 33/542* (2013.01); *G01N 33/569* (2013.01); *C09K 2211/185* (2013.01); *G01N 21/07* (2013.01); *G01N 21/6452* (2013.01); *G01N 2021/6432* (2013.01); *G01N 2021/7786* (2013.01)

(58) Field of Classification Search
CPC ........................................................ C12Q 1/04
See application file for complete search history.

(56) References Cited

U.S. PATENT DOCUMENTS

| | | |
|---|---|---|
| 5,567,598 A | 10/1996 | Stitt et al. |
| 8,759,110 B2 | 6/2014 | Geddes |
| 2005/0054028 A1 | 3/2005 | Teich et al. |
| 2009/0296083 A1 | 12/2009 | Saaski et al. |
| 2010/0227773 A1 | 9/2010 | Abel et al. |
| 2012/0021034 A1 | 1/2012 | Zink et al. |
| 2012/0270261 A1 | 10/2012 | Mayer et al. |
| 2014/0017810 A1 | 1/2014 | Kimura |
| 2015/0060698 A1 | 3/2015 | Mozolowski et al. |
| 2015/0118707 A1 | 4/2015 | Selvaganapathy |

FOREIGN PATENT DOCUMENTS

WO  2013122852 A1  8/2013

OTHER PUBLICATIONS

Kocinocova et al. Biotechnology and Bioengineering, 2008, 100:430-438.*
Kuhl et al. Applied and Environmental Microbiology, 2007, 73(19):6289-6295.*
Phillips et al. Angew. Chem. Int. Ed., 2008, 47:2590-2594.*
Ravindranath et al. Anal. Chem., 2009, 81:2840-2846.*
International Search Report in the parent PCT application No. PCT/US2016/038440, dated Sep. 13, 2016.
IPRP in the parent PCT application No. PCT/US2016/038440, dated Dec. 26, 2017.
Ayyash et al., "Fast and inexpensive detection of bacterial viability and drug resistance through metabolic monitoring", IEEE, 2014 Health Innovations and Point-of-Care Technologies Conference, Seattle, Washington, Oct. 8-10, 2014, pp. 22-25.
Brouard et al., "Label-Free Biosensing Based on Multilayer Fluorescent Nanocomposites and a Cationic Polymeric Transducer", ACS NANO, 2011, vol. 5, No. 3, pp. 1888-1896.
Extended European Search Report, dated May 11, 2018 in corresponding application EP 16815118.1.
Chinese Office Action, dated Feb. 12, 2019, and Search Report dated Jan. 30, 2019, in a counterpart Chinese patent application, No. CN 201680037373.3.
Fanbin et al., "Progress in Metal Enhanced Fluorescence in Aqueous Solution", Chemistry, vol. 78, No. 6, pp. 489-496, Jun. 18, 2015. (English abstract included).

* cited by examiner
(Continued)

*Primary Examiner* — Bin Shen
(74) *Attorney, Agent, or Firm* — Chen Yoshimura LLP (57) ABSTRACT

An improved method and related apparatus for detecting bacteria viability and drug effects using metabolic monitoring. A fluorescent material which is quenched by oxygen is co-localized with the target bacteria, and fluorescence signal is detected at the co-localized places. In some embodiments, the fluorescent material is a fluorescent nanoparticle mixed with the target bacteria in the sample, and co-localization is enhanced using centrifugation, electrophoresis, microflow path modified with antibodies, magnetic force, etc. In some other embodiments, the fluorescent material is a fluorescent film or 3-D matrix immobilized in the bacterial culture chamber, and bacteria in the sample is gathered into localized regions of the bacteria culture chamber where the fluorescent film or 3-D matrix is present by ways of centrifugation, electrophoresis or microflow path. Plasmonic nanoparticles with a metal core and plasmonic film with a metal film may be used as the fluorescent nanoparticles and fluorescent film.

6 Claims, 7 Drawing Sheets

RAPID AND HIGH-SENSITIVE BACTERIA DETECTION

BACKGROUND OF THE INVENTION

Field of the Invention

This invention relates to bacteria detection such as bacterial viability and drug resistance through metabolic monitoring, and in particular, it relates to bacteria detection using oxygen sensitive fluorescent materials and methods for enhancing co-localization of the bacteria and the fluorescent materials.

Description of Related Art

A rapid bacteria detection technology using micro-well array and oxygen sensitive fluorescent film is described in Ayyash et al., Fast and inexpensive detection of bacterial viability and drug resistance through metabolic monitoring, 2014 Health Innovations and Point-of-Care Technologies Conference (Seattle, Wash. USA) Oct. 8-10, 2014 ("Ayyash et al. 2014"). In this technology, oxygen consumption in the well including the bacteria leads to fluorescent signal emission. Excerpts of the paper are presented below:

[We introduce] an innovative detection method to produce rapid and accurate diagnosis of bacterial infection through miniaturization and parallelization. This method is demonstrated with wells of several shapes (square, circle), diameters (100-1000 µm) and depths (≤100 µm). In the development of proof of concept, we use laboratory strain of *E. coli* as the model pathogen. The integration of the fluorescent oxygen sensor, ruthenium tris (2,2'-diprydl) dichloride hexahydrate (RTDP), allows us to monitor the dissolved oxygen concentration as a measure of bacterial metabolism. Detection time of the bacteria within the microwells can be as fast as a few of hours (4-5 hrs), with concentrations that vary between 102 to 108 cells/mL. Adding the appropriate drug to the broth and measuring growth through fluorescence also probed drug resistance. This reported method for microfabrication of the wells, is rapid, economical, versatile and simple. (Abstract.)

In this method, the sample is placed in a chamber with a growth medium that is specific for the particular bacteria of interest. This liquid medium provides a specific condition for the growth of the specific bacteria of interest while preventing other contaminating species from growing. A fluorophore that is quenched in the presence of oxygen is dissolved in the medium. Since bacteria are aerobic, they consume oxygen that is present in the medium during metabolism and depletes the oxygen in the surrounding environment, producing fluorescence. Drug resistance can be probed by adding the appropriate drug to the broth and measuring growth or lack of it through fluorescence. (Pp. 22-23.)

When this metabolic monitoring is done in large volumes (1-10 mL) it still takes a long time. However if the sample were segmented into thousands of smaller volumes then some of the wells will contain the bacteria of interest while others will not. The process of segmentation will increase the local concentration of the bacteria by several orders of magnitude. Therefore the nutrients present in that small volume will be quickly depleted and that event can be sensed faster. This is the working principle behind our fast metabolic monitoring of bacteria. (P. 23.)

Experimental Setup and Procedure. In a typical experiment, the sample is mixed with a solution containing the growth medium (Luria-Bertani (LB) medium) and an oxygen sensitive fluorophore (ruthenium tris(2,2'-diprydl) dichloride hexahydrate, (RTDP)-0.1 mg/mL) and dispensed on to the microarray. A simple swiping process dispenses the sample into the hydrophilic microwells while the hydrophobic top surface removes the sample from the top cleanly (step 4,5 in FIG. 1). Next, the microarray is capped using a glass slide (made hydrophobic using a surfactant) and imaged under a fluorescent microscope to measure the intensity of the fluorophore. (P. 23.)

Figure 1:
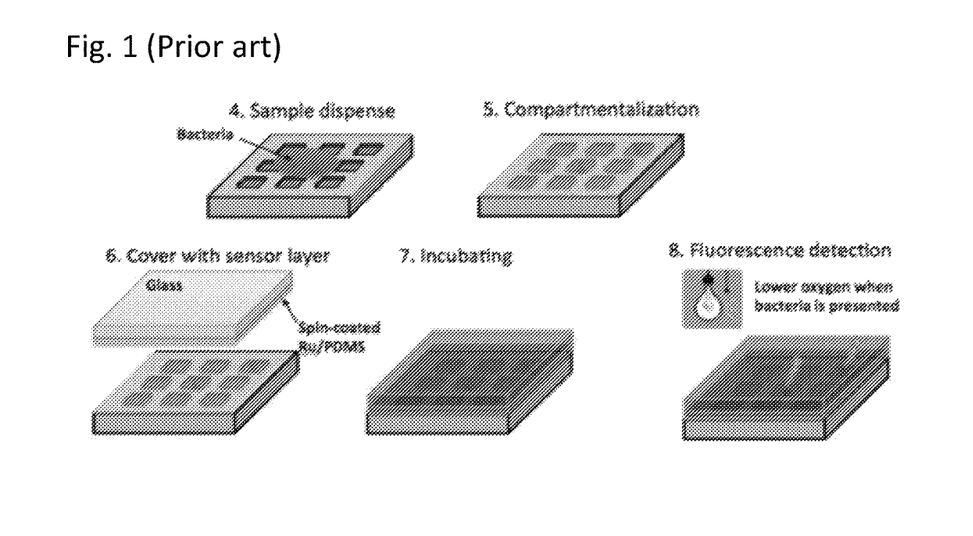
FIGS. 1 and 1A schematically illustrate a bacteria detection method using micro-well array and oxygen sensitive fluorescent film.
Figure 1A:
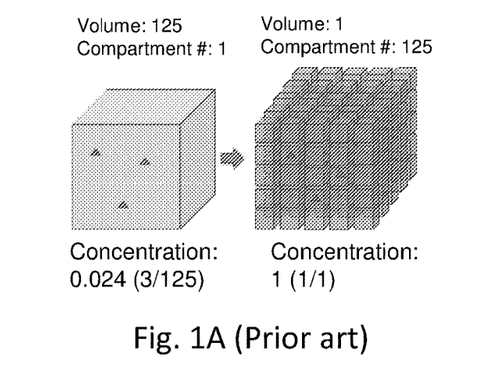

Part of FIG. 1 of Ayyash et al. 2014 is reproduced in FIG. 1 of the instant application. FIG. 1A of the instant application schematically illustrates an example of segmentation described in Ayyash et al. 2014, which increases the local concentration of the bacteria and oxygen is depleted quickly.

SUMMARY

In the detection technique described in Ayyash et al. 2014, since there is a distance between the location where oxygen is consumed by bacteria and the fluorescent film, the oxygen consumption does not lead to immediate fluorescent signal emission by the fluorescent film.

Embodiments of the present invention provides an improved, rapid and highly-sensitive bacteria detection method using co-localization of bacteria and a fluorescent material which is quenched by oxygen. The fluorescent material optionally has an affinity with the target bacteria.

An object of this invention is to improve turnaround time for bacteria detection. It can realize rapid detection with high sensitivity.

Additional features and advantages of the invention will be set forth in the descriptions that follow and in part will be apparent from the description, or may be learned by practice of the invention. The objectives and other advantages of the invention will be realized and attained by the structure particularly pointed out in the written description and claims thereof as well as the appended drawings.

To achieve these and/or other objects, as embodied and broadly described, the present invention provides a method for detecting live bacteria, which includes: providing a fluorescent material which is quenched by oxygen; co-localizing the fluorescent material with the bacteria in a region of a bacteria culture chamber; allowing the bacteria to grow; and detecting a fluorescence signal emitted by the fluorescent material in the co-localized region.

The fluorescent material may be fluorescent nanoparticles or fluorescent film, and may have an affinity to the bacteria. Co-localization may be achieved using centrifugation, electrophoresis, microflow path, magnetic field, 3-D matrix, etc.

In another aspect, the present invention provides a material useful in bacteria detection, including fluorescent molecules which are quenched by oxygen, and further having an affinity to the target bacteria.

It is to be understood that both the foregoing general description and the following detailed description are exemplary and explanatory and are intended to provide further explanation of the invention as claimed.

DETAILED DESCRIPTION OF PREFERRED EMBODIMENTS

Embodiments of the present invention provide bacteria detection methods which co-localize bacteria and a fluorescent material that includes fluorescent molecules quenched by oxygen. In some embodiments, the fluorescent material also has an affinity with the target bacteria or cells. Since the distance between the oxygen-sensitive fluorescent material and the bacteria is close, oxygen consumption by the bacteria immediately leads to fluorescent signal emission from the fluorescent material. Thus, rapid and highly-sensitive bacteria detection is realized.

Figure 2:
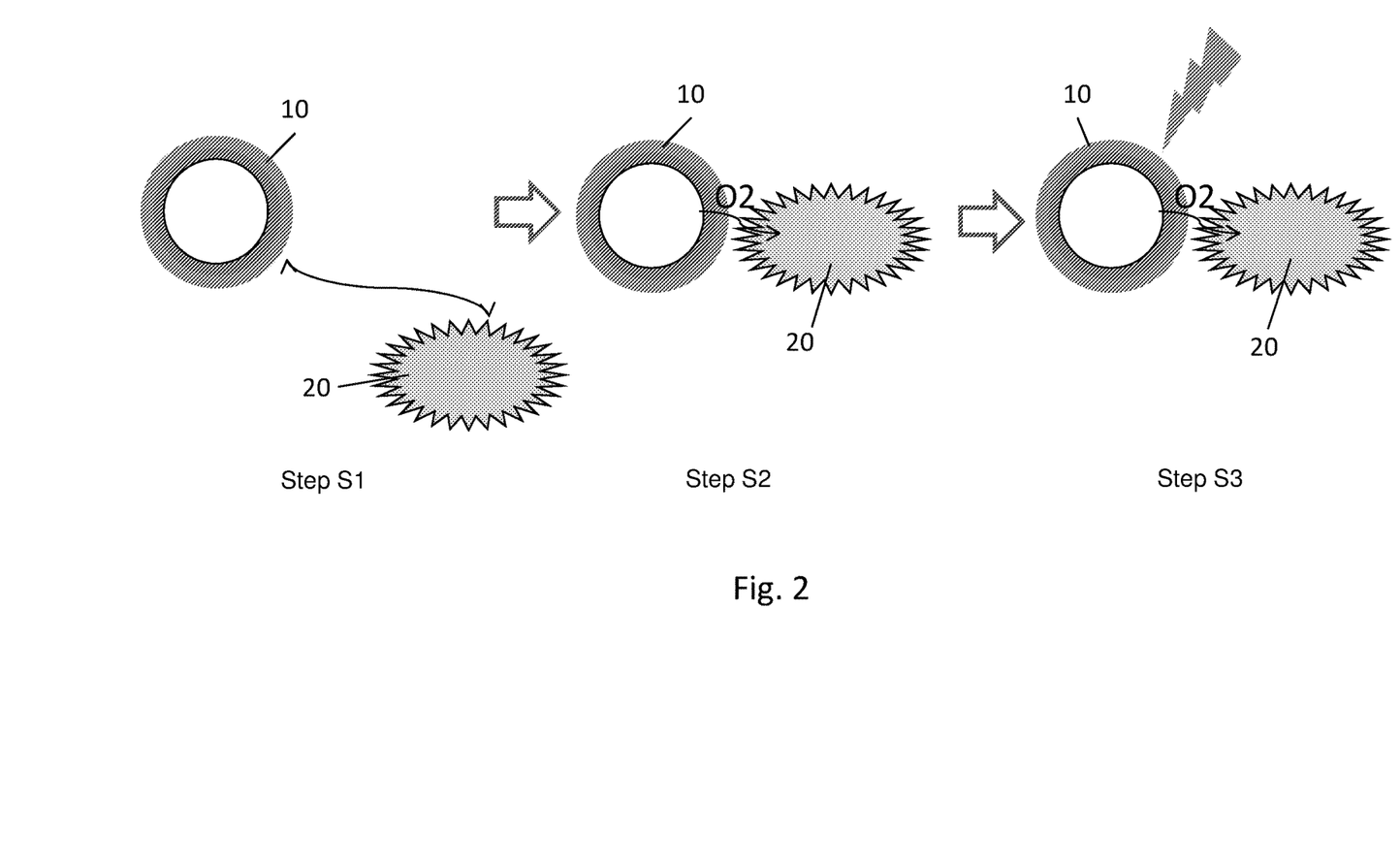
FIG. 2 schematically illustrates the principle of bacteria detection according to embodiments of the present invention.

FIG. 2 schematically illustrates the principle of bacteria detection according to embodiments of the present invention. The bacteria detection method uses a fluorescent material 10 which includes fluorescent molecules quenched by oxygen. The fluorescent material 10 is co-localized with live bacteria 20 (step S1), via co-localization mechanisms described in more detail later. The bacteria 20 are allowed to grow and consume oxygen (step S2), which deprives oxygen from the adjacent fluorescent material 10; as a result, the fluorescent material emits a fluorescence signal. The fluorescence signal from the co-localized place is detected (step S3). The setup described in Ayyash et al. 2014 for detecting the fluorescence signal may be used in step S3, or any other suitable setup may be used.

Figure 3A:
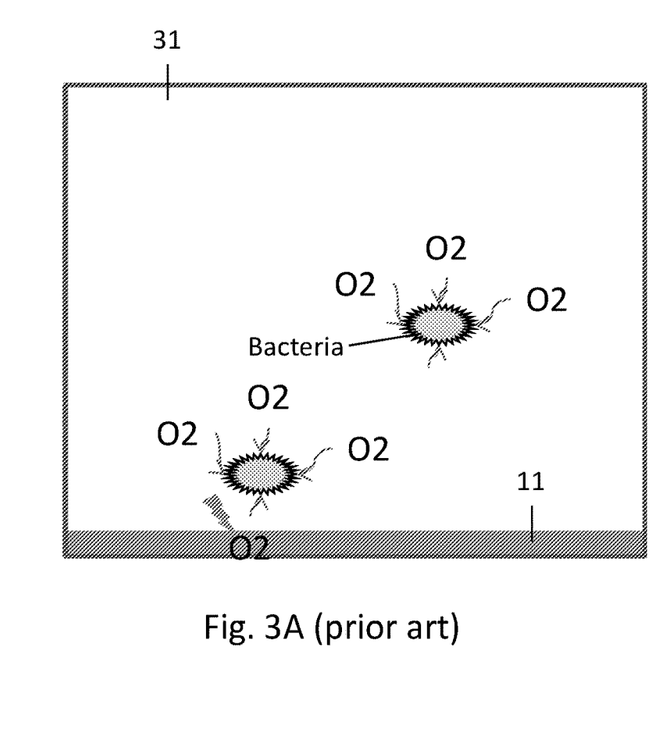
FIGS. 3A and 3B schematically illustrate the advantages of co-localization of fluorescent nanoparticles with bacteria according to embodiments of the present invention.
Figure 3B:
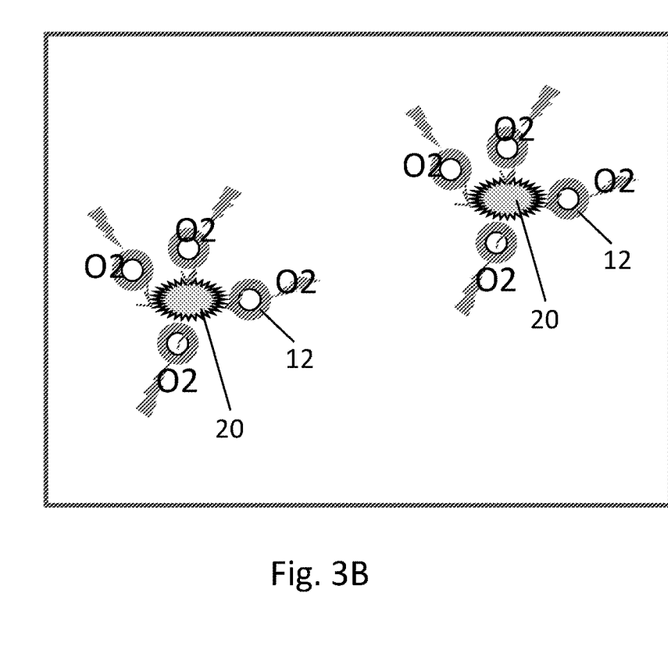

In some embodiments, the fluorescent material is a fluorescent nanoparticle that is mixed in the sample containing the target bacteria. The fluorescent nanoparticle may be formed of a core coated with the fluorescent molecules which are quenched by oxygen. In some embodiments, the fluorescent nanoparticle has an affinity to the target bacteria. The sample containing target bacteria and the fluorescent material is introduced into a bacteria culture chamber, such as microwells or a microfluidic device. FIGS. 3A and 3B schematically illustrate the advantages of co-localization of the fluorescent nanoparticles with the bacteria. FIG. 3A schematically illustrates a microwell 31 with a fluorescent film 11 coated on its bottom (as described in Ayyash et al. 2014), and a sample containing the target bacteria 20 in the microwell. FIG. 3B illustrates fluorescent nanoparticles 12 which surround the bacteria 20 in a sample according to embodiments of the present invention. Since the nanoparticles 12 can surround the bacteria 20, the chances of the oxygen deprival from the nanoparticles are increased, and thus the fluorescence signal is enhanced as compared to the case where a fluorescent film is used (FIG. 3A).

Various mechanisms may be used to enhance co-localization of the fluorescent nanoparticles 12 with target bacteria 20, some of which are described below with reference to FIGS. 4A-D.

Figure 4A:
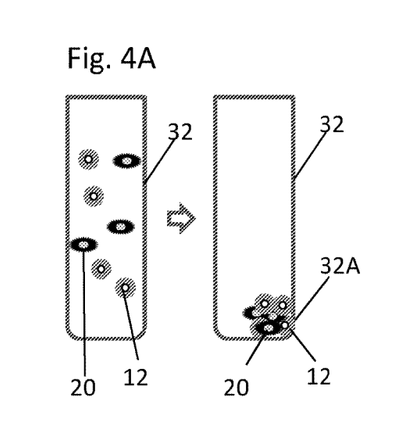
FIGS. 4A to 4D schematically illustrate mechanisms for achieving or enhancing co-localization of fluorescent nanoparticles with target bacteria according to embodiments of the present invention.

A first co-localization method uses centrifugation (FIG. 4A). A sample containing the target bacteria 20 and the fluorescent nanoparticles 12 is placed in a bacteria culture chamber 32 (e.g. a centrifuge tube) and spun in a centrifuge (not shown). As a result, both the bacteria 20 and the fluorescent nanoparticles 12 are gathered in a bottom region 32A of the centrifuge tube by centrifugal force, where they are in close proximity to each other (i.e. co-localized).

Figure 4B:
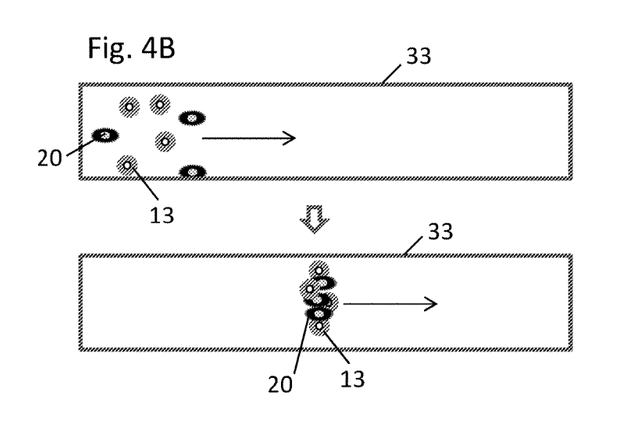

A second co-localization method uses electrophoresis in a microfluidic device 33 (FIG. 4B). The fluorescent nanoparticles 13 are selected to have similar electro mobility properties as the target bacteria. A sample containing the bacteria 20 and nanoparticles 13 is introduced in the microfluidic device 33, where an electrical field is applied. The bacteria and nanoparticles are focused by the electrical field in the same regions of the microfluidic device, where they are in close proximity to each other (i.e. co-localized).

Figure 4C:
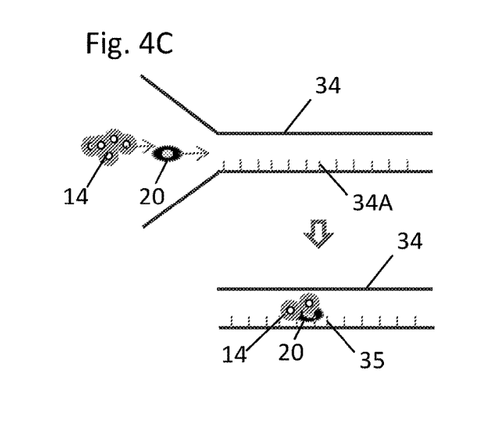

A third co-localization method uses a microfluidic device, where the microflow path 34 is modified with a capture material 3A which has an affinity to the bacteria (such as an antibody) (FIG. 4C). The microflow path 34 may be a constricted segment of a microfluidic device. The fluorescent nanoparticles 14 in this embodiment also have an affinity to the bacteria; for example, they may have antibodies on their surfaces. As the sample containing the target bacteria 20 and the fluorescent nanoparticles 14 flows through the microflow path 34, the bacteria 20 are trapped in the path by the capture material 34A. The fluorescent nanoparticles 14 are trapped by the bacteria 20 in the microflow path 34 in the vicinity of the bacteria, so that the fluorescent nanoparticles and the bacteria are in close proximity to each other (i.e. co-localized).

Figure 4D:
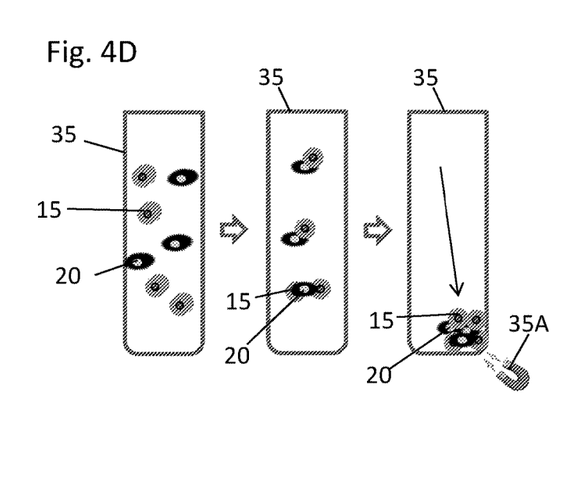

A fourth co-localization method uses a fluorescent nanoparticle 15 which also has paramagnetism (FIG. 4D). The fluorescent nanoparticles 15 in this embodiment also have an affinity to the bacteria. The sample containing the bacteria 20 and the fluorescent nanoparticles 15 is placed in a bacteria culture chamber 35 and mixed, and the bacteria are trapped by the magnetic nanoparticles. A magnetic field is applied to the bacteria culture chamber 35 by a magnetic element 35A, and the magnetic nanoparticles 15 and the bacterial 20 are gathered by the magnetic force to one end of the bacteria culture chamber, so that the magnetic nanoparticles and the bacteria are in close proximity to each other (i.e. co-localized).

For the third and fourth co-localization methods described above (microflow path, FIG. 4C, and magnetic force, FIG. 4D), the fluorescent nanoparticles are required to have an affinity to the bacteria. For the first and second co-localization methods (centrifugation, FIG. 4A, and electrophoresis, FIG. 4B), an affinity between the fluorescent nanoparticles and bacteria is not required, but is helpful for enhancing the co-localization effect. Using fluorescent nanoparticles that have an affinity to the bacteria also stabilize the co-localization of the fluorescent nanoparticles and the bacteria.

The above described co-localization methods (FIGS. 4A-4D) may be used in combination with each other.

In some other embodiments, the oxygen-sensitive fluorescent material is a fluorescent film or other material immobilized on the bacteria culture chamber or microflow path, and mechanisms are provided to promote the co-localization of the bacteria and the immobilized fluorescent material. Some examples are described below with reference to FIGS. 5A-5D.

Figure 5A:
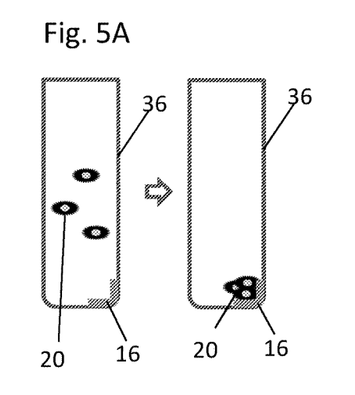
FIGS. 5A to 5D schematically illustrate mechanisms for achieving or enhancing co-localization of immobilized fluorescent material with target bacteria according to embodiments of the present invention.

A first co-localization method uses centrifugation (FIG. 5A). A fluorescent film 16 is immobilized in a bottom region of the bacteria culture chamber 36 (the centrifuge tube). The sample containing the target bacteria 20 is placed in the centrifuge tube 36 and spun in the centrifuge (not shown). As a result, bacteria 20 are gathered in a bottom region of the centrifuge tube by centrifugal force and are located in close proximity of the fluorescent film 16 (i.e. they are co-localized).

Figure 5B:
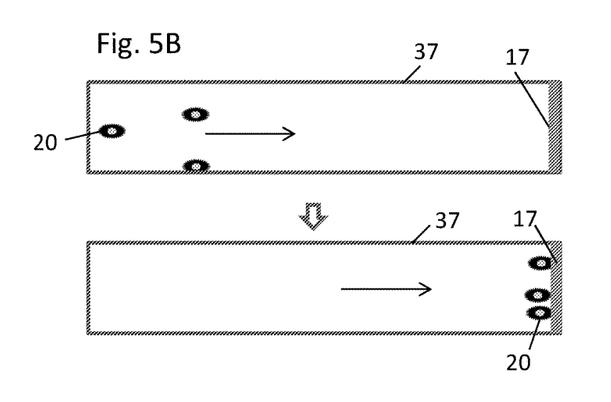

A second co-localization method uses electrophoresis (FIG. 5B). A fluorescent film 17 is immobilized on an end wall of the bacteria culture chamber 37. The sample containing the target bacteria 20 is placed in the bacteria culture chamber 37 and an electrical field is applied, causing the bacteria to move toward that end wall and are gathered there, so that the bacteria are located in close proximity of the fluorescent film 17 (i.e. they are co-localized).

Figure 5C:
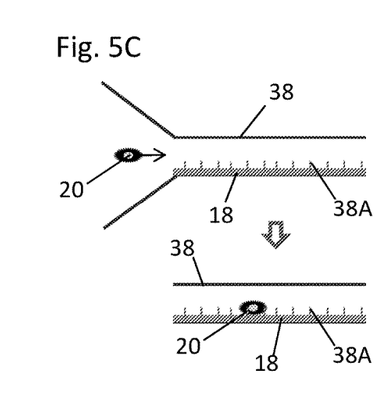

A third co-localization method uses a microfluidic device 38, where the side surface of the microflow path is modified with a fluorescent material 18 (FIG. 5C). The same side surface of the microflow path is also modified with a material 38A that has an affinity to the bacteria, such as an antibody. When the bacteria 20 pass through the microflow path, they are trapped in the path by the antibodies 38A, so that the bacteria are located in close proximity of the fluorescent material 18 (i.e. they are co-localized).

Figure 5D:
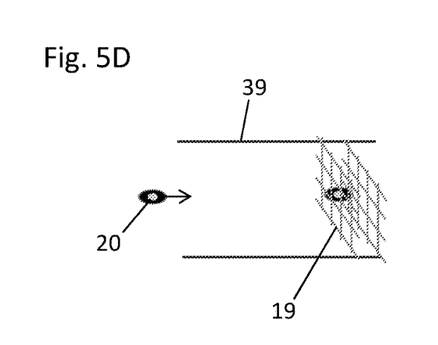

A fourth co-localization method uses a microfluidic device 39 having a 3-D matrix 19 in the microflow path of the microfluidic device (FIG. 5(D)). The 3-D matrix 19 is made of a base material such as carboxyl methyl dextran, which is modified with a fluorescent material coating as well as a material that has an affinity to the bacteria such as an antibody. When bacteria 20 pass through the matrix 19, they are trapped in the 3-D matrix by the antibody, so that the bacteria are located in close proximity of the fluorescent material (i.e. they are co-localized).

For the third and fourth co-localization methods described above, the microflow path surface 18 and the 3-D matrix 19 are required to have an affinity to the bacteria. For the first and second co-localization methods (centrifugation and electrophoresis), a material with an affinity to the bacteria is not required for the fluorescent films 16 and 17, but is helpful for enhancing the co-localization effect. Using fluorescent materials that have an affinity to the bacteria also stabilize the co-localization of the fluorescent materials and the bacteria.

The above described co-localization methods (FIGS. 5A-5D) may be used in combination with each other.

Another advantage of the embodiments using immobilized fluorescent material is that since the bacteria are gathered to the place where the fluorescent material is immobilized, additional fluorescent material gathering process or mechanism is not required.

All of the above co-localization method (FIGS. 4A-4D and FIGS. 5A-5D) achieve the result that the bacteria and the fluorescent nanoparticles or the immobilized fluorescent materials are located in close proximity to each other, so that the effect of oxygen deprivation caused by the bacteria on the fluorescent material is enhanced. The fluorescent molecules in the fluorescent nanoparticles or the immobilized fluorescent materials are ones that are quenched by oxygen.

In the embodiments that use fluorescent nanoparticles (e.g. FIGS. 4A-4D) and fluorescent film (e.g. FIGS. 5A-5D), the fluorescence signal of the particles and film may be further enhanced using the principle of metal-enhanced fluorescence (MEF). MEF refers to the phenomenon that the intensity of fluorescence signal is increased when the fluorescent material is in the proximity of a metal.

Figure 6A:
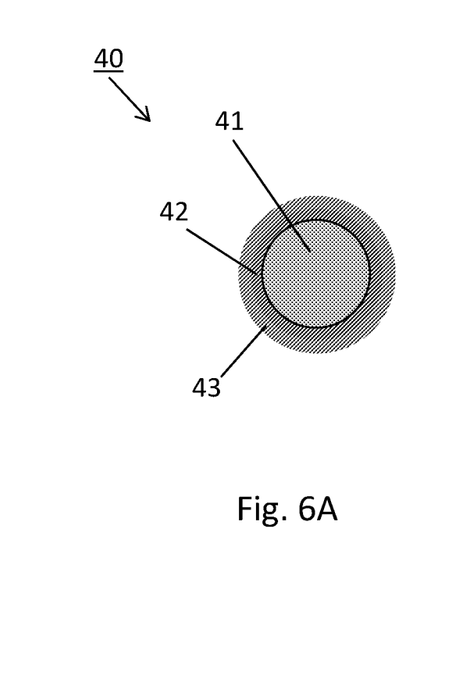
FIG. 6A schematically illustrates the structure of a fluorescent nanoparticle having a metal core.
Figure 6B:
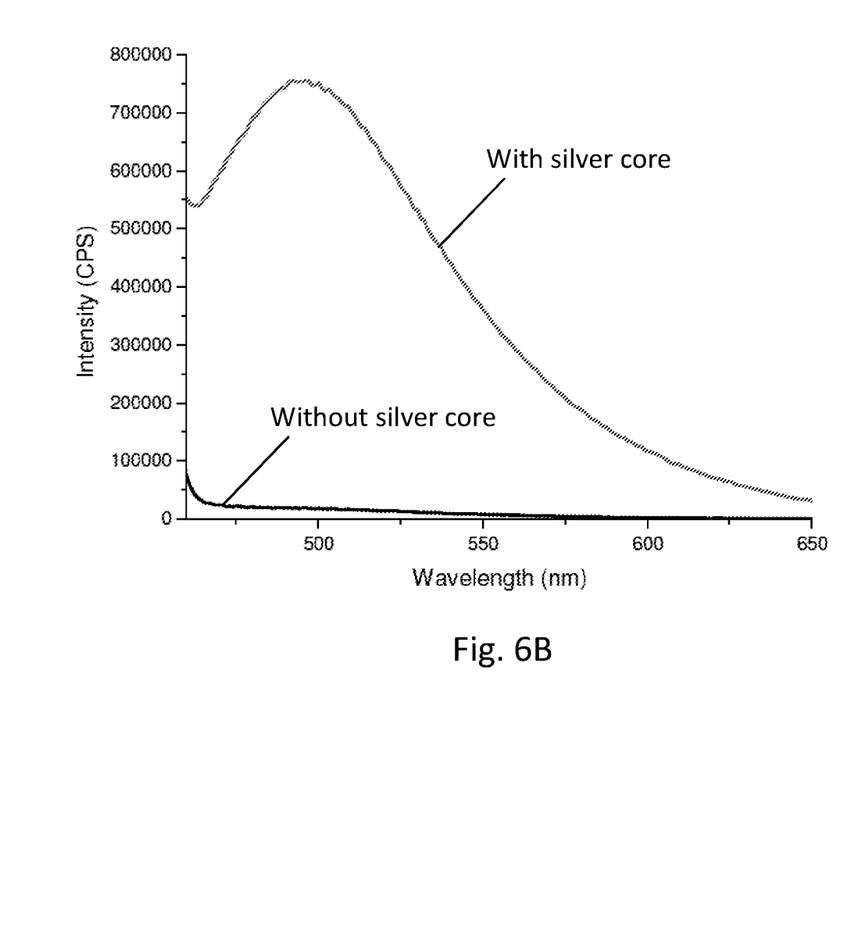
FIG. 6B shows fluorescent signals enhancement by using plasmonic nanoparticles with a metal core.

In the case of fluorescent nanoparticles, FIG. 6A schematically illustrates the structure of a fluorescent nanoparticle 40 having a metal core, referred to as a plasmonic nanoparticle. The fluorescent nanoparticle 40 is formed of a metal core 41, a spacer layer 42 outside the metal core, and a fluorescent material layer 43 outside the spacer layer. The metal for the metal core 41 may be gold, silver, aluminum, etc. The spacer layer 42 may be made of silica or other suitable material. The fluorescent material 43 is one that is quenched by oxygen. Preferably, ruthenium tris (2,2'-dipyrdyl) dichloride hexahydrate (RTDP, excitation wavelength: 460 nm, emission wavelength: 600 nm) is used as the fluorescent material, in which case silver is the preferred metal for MEF. As shown in FIG. 6B, at wavelengths of 500 nm and above, the fluorescence signals of the plasmonic nanoparticles may be 30 times the fluorescence signals emitted by nanoparticles without the metal core. Plasmonic nanoparticles are known; they have been described in, for example, U.S. Pat. No. 8,759,110, and D. Brouard et al., Label-Free Biosensing Based on Multilayer Fluorescent Nanocomposites and a Cationic Polymeric Transducer, ACS NANO, VOL. 5, NO. 3, 1888-1896 (2011).

In the case of fluorescent film or coating, such as those in the embodiments shown in FIGS. 5A-5D, to take advantage of MEF, the film may be formed of multiple layers including a metal layer on the surface of the bacteria culture chamber or the 3-D matrix, a spacer layer on the metal layer, and a fluorescent material layer on the spacer layer. The same materials as mentioned above for the plasmonic nanoparticle may be used for the various layers of the fluorescent film here.

Figure 7A:
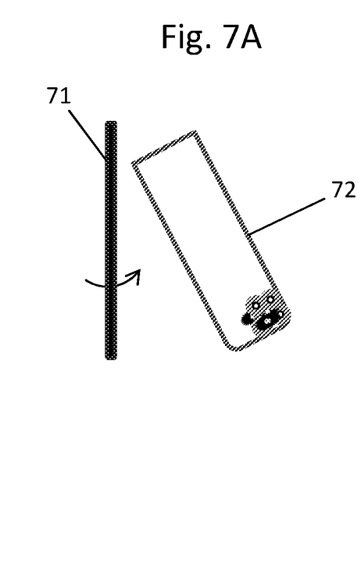
FIGS. 7A to 7D schematically illustrate improved centrifugation devices that can be applied in the embodiments of FIG. 4A.
Figure 7B:
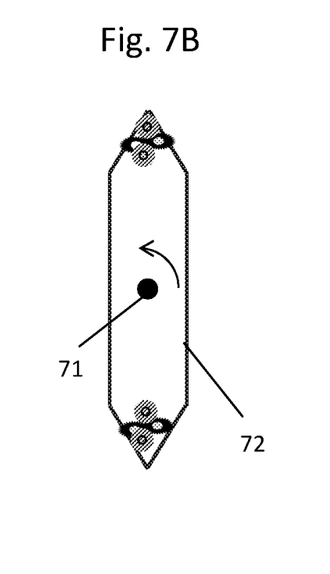
Figure 7C:
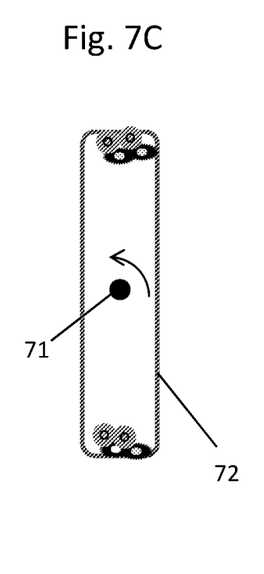
Figure 7D:
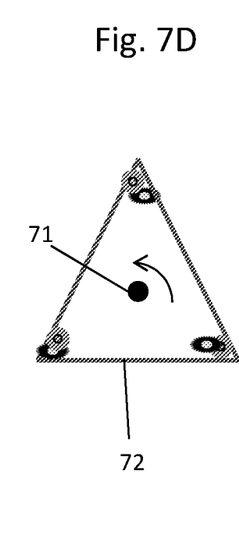

FIGS. 7A-7D schematically illustrate improved centrifugation devices that can be applied in the embodiment of FIG. 4A to further enhance the co-localization of bacteria and fluorescent nanoparticles. FIG. 7A shows a conventional centrifugation device, where the centrifuge tube 72 is disposed at an acute angle with respect to the rotation axis 71. FIG. 7A is a side view where the rotation axis is in the plane of the drawing sheet. FIG. 7B-7D illustrate three examples of alternative centrifugation devices, in a top view where the rotation axis 71 is perpendicular to the plane of the drawing sheet. In the top view, the centrifuge containers 72 are symmetrical in shape with respect to the rotation axis 71. In FIGS. 7B and 7D, the centrifuge container 72 is a tube shape or triangle shape, respectively, which respectively has two or three narrow ends where the bacteria and nanoparticles can be concentrate into small volumes. Other suitable shapes with narrow ends may also be used.

In the various embodiments described above, the bacteria culture chamber is preferably as small as possible to avoid oxygen capturing from materials other than the fluorescent materials (fluorescent nanoparticles or immobilized fluorescent materials).

It will be apparent to those skilled in the art that various modification and variations can be made in the bacteria detection method and related apparatus of the present invention without departing from the spirit or scope of the invention. Thus, it is intended that the present invention cover modifications and variations that come within the scope of the appended claims and their equivalents.

What is claimed is:

1. A method for detecting live bacteria, comprising:
providing a fluorescent material which is quenched by oxygen, the fluorescent material comprising fluorescent nanoparticles;
co-localizing the fluorescent nanoparticles with the bacteria in a region of a bacteria culture chamber, wherein the co-localizing step includes one or more of:
(1) applying centrifugation to a sample containing the bacteria and the fluorescent nanoparticles,
(2) applying electrophoresis to a sample containing the bacteria and the fluorescent nanoparticles, wherein the fluorescent nanoparticles have same mobility as the bacteria,
(3) passing a sample containing the bacteria and the fluorescent nanoparticles through a microflow path, wherein a surface of the microflow path is modified with an antibody which has an affinity to the bacteria and wherein the fluorescent nanoparticles have an affinity to the bacteria, or
(4) applying a magnetic field to a sample containing the bacteria and the fluorescent nanoparticles, wherein the fluorescent nanoparticles have paramagnetism and have an affinity to the bacteria;
allowing the bacteria to grow; and
detecting a fluorescence signal emitted by the fluorescent nanoparticles in the co-localized region.

2. The method of claim 1, wherein each fluorescent nanoparticle comprises:
a metal core;
a spacer layer outside the metal core; and
a fluorescent material outside the spacer layer.

3. The method of claim 2, wherein the metal core is made of gold, silver, or aluminum.

4. A method for detecting live bacteria, comprising:
providing a fluorescent material which is quenched by oxygen;
co-localizing the fluorescent material with the bacteria in a region of a bacteria culture chamber, wherein the co-localizing step includes one of:

(1) providing a bacteria culture chamber which has a surface region with the fluorescent material formed on it as a film, placing a sample containing the bacteria in the bacteria culture chamber, and applying centrifugation to the bacteria culture chamber to collect the bacteria in the region where the fluorescent film is located,
(2) providing a bacteria culture chamber which has a surface region with the fluorescent material formed on it as a film, placing a sample containing the bacteria in the bacteria culture chamber, and applying electrophoresis to the bacteria culture chamber to collect the bacteria in the region where the fluorescent film is located,
(3) providing a microfluidic device which has a microflow path with the fluorescent material formed as a film on its surface, the surface of the microflow path being further modified with an antibody that has an affinity to the bacteria, and flowing a sample containing the bacteria through the microflow path, or
(4) providing a microfluidic device which has a microflow path with a 3-D matrix placed in it, the 3-D matrix having the fluorescent material formed on it as a coating, the 3-D matrix being further modified with a capture material that has an affinity to the bacteria, and flowing a sample containing the bacteria through the 3-D matrix in the microflow path;
allowing the bacteria to grow; and
detecting a fluorescence signal emitted by the fluorescent material in the co-localized region.

5. The method of claim 4, wherein the fluorescent film or coating comprises:
a metal layer;
a spacer layer on the metal layer; and
a fluorescent material layer on the spacer layer.

6. The method of claim 5, wherein the metal layer is made of gold, silver, or aluminum.

* * * * *